United States Patent [19]

Drent

[11] Patent Number: 5,214,220
[45] Date of Patent: May 25, 1993

[54] PROCESS FOR THE PREPARATION OF ALCOHOLS

[75] Inventor: Eit Drent, Amsterdam, Netherlands

[73] Assignee: Shell Oil Company, Houston, Tex.

[21] Appl. No.: 926,534

[22] Filed: Aug. 10, 1992

[30] Foreign Application Priority Data

Aug. 30, 1991 [GB] United Kingdom ............... 9118603

[51] Int. Cl.$^5$ ............................................. C07C 29/141
[52] U.S. Cl. ..................................... 568/881; 568/880; 568/884; 568/885; 568/876
[58] Field of Search ............... 568/814, 880, 881, 882, 568/883, 884, 885, 876

[56] References Cited

U.S. PATENT DOCUMENTS

| 3,454,644 | 7/1969 | Dewhirst ........................... 568/881 |
| 3,458,547 | 7/1969 | Stevenson et al. ................. 568/881 |
| 4,263,449 | 4/1981 | Saito et al. . |
| 4,481,375 | 11/1984 | Kalk et al. ......................... 568/883 |
| 4,517,390 | 5/1985 | Russell et al. ..................... 568/883 |
| 4,684,750 | 8/1987 | Kessen et al. ..................... 568/883 |
| 5,041,683 | 8/1991 | Marhold et al. ................... 568/425 |

FOREIGN PATENT DOCUMENTS

| 2145033 | 6/1987 | Japan ................................. 568/882 |
| 2298543 | 12/1987 | Japan ................................. 568/882 |
| 1270985 | 9/1969 | United Kingdom . |

*Primary Examiner*—Werren B. Lone

[57] ABSTRACT

The invention relates to a process for the preparation of an alcohol by hydrogenation of an aldehyde at elevated temperature and superatmospheric pressure in the presence of a homogeneous catalytic system comprising a source of a Group VIII metal compound and a bidentate phosphine.

12 Claims, No Drawings

PROCESS FOR THE PREPARATION OF ALCOHOLS

FIELD OF THE INVENTION

This invention relates to a process for the preparation of an alcohol by hydrogenation of an aldehyde at elevated temperature and superatmospheric pressure in the presence of a homogeneous catalytic system.

BACKGROUND OF THE INVENTION

Catalyst systems which have been proposed for this process, include catalysts based on soluble Group VIII metal compounds, for example of cobalt or rhodium.

Aldehyde precursors for use in this process may, for instance, be obtained by hydroformylation of an olefinically unsaturated compound in the presence of a Group VIII metal catalyst, which process has attained industrial application and is also known as the oxo process. Frequently, the aldehyde produced by hydroformylation of an olefin is separated from the reaction mixture obtained by the hydroformylation to eliminate the catalyst and by-products and is subsequently used in the hydrogenation.

U.S. Pat. No. 4,263,449 discloses a process for the preparation of alcohols, wherein the aldehyde-containing reaction product of a hydroformylation reaction is used as such in a subsequent hydrogenation reaction catalyzed by a heterogeneous Raney nickel or cobalt catalyst. Water is added for generating a biphasic reaction product facilitating separation of the catalysts used. Apart from the inherent complications of the use of a plurality of catalysts, the use of active Raney catalysts will concurrently hydrogenate any olefin values remaining in the hydroformylation product.

According to Great Britain Patent No. 1,270,985, cobalt carbonyls modified by tertiary phosphines, known to be active as hydroformylation catalyst, can be used in the hydrogenation of aldehydes to alcohols under an atmosphere comprising both hydrogen and carbon monoxide. However, high reaction temperatures and pressures are required for this process.

Other known hydrogenation processes require a pure hydrogenation atmosphere, so that carbon monoxide should be removed, if an aldehyde-containing hydroformylation product is to be directly used.

A catalytic system comprising a compound of palladium and a bidentate phosphine is described by Y. Ben David et al., in J. Am. Chem. Soc., 1989, 111, 8742-4, but only for use in the carbonylation of aryl chlorides.

Therefore, there remains a continued need for improved and more versatile catalysts for the hydrogenation of aldehydes.

SUMMARY OF THE INVENTION

The present invention relates to the hydrogenation of aldehydes to alcohols in the presence of a homogeneous catalytic system comprising a source of a Group VIII metal compound and a bidentate phosphine.

The catalyst system used according to the invention offers the advantages of high activity at mild conditions of temperature and/or pressure, applicability in the presence or absence of carbon monoxide in the hydrogenation atmosphere, and a remarkable selectivity in that unsaturated compounds such as olefins or ketones remain substantially unaffected under conditions where aldehydes are readily hydrogenated to alcohols.

DESCRIPTION OF THE PREFERRED EMBODIMENTS

Aldehydes which are used for the hydrogenation are preferably aliphatic aldehydes having 2 to about 20 carbon atoms. They may contain one or more aldehyde groups, and also substituents which are inert under the reaction conditions, such as aryl groups, hydroxy groups, carboxy groups, $C_{1-4}$ alkoxy groups, or ester groups having 1 to about 7 carbon atoms. Aldehydes having 3 to about 20 carbon atoms which have been prepared by oxo synthesis are particularly suitable. Suitable examples include propanal, butanal, 2-methylpropanal, 4-hydroxybutanal, 6-oxohexanoic esters, octanal, nonyl aldehydes, tridecanals or 2-ethylhexanal.

The hydrogenation is carried out in the presence of a catalytic system comprising a Group VIII metal which is preferably selected from palladium, platinum, and rhodium, and mixtures thereof, with palladium being particularly preferred. The Group VIII metal catalyst component may be provided in the form of a Group VIII metal salt such as salts of nitric acid; sulfuric acid; sulfonic acids, for example trifluoromethane sulfonic acid or paratoluene sulfonic acid; and carboxylic acids, for example acetic acid or trifluoro acetic acid. The Group VIII metal salt may be in the form of a complex, for example with a phosphine and/or other ligand. The Group VIII metal may also be provided in the form of the metallic element or a zero valent complex with a ligand such as a phosphine or carbon monoxide. If provided in metallic form, it should be used with a protonic acid for formation in situ of a soluble salt or complex.

The quantity of the Group VIII metal is not critical. Preferably, it is in the range of about $10^{-7}$ to about $10^{-1}$ gram atom of Group VIII metal per mole of aldehyde substrate, more preferably from about $10^{-6}$ to about $10^{-2}$.

The second essential component of the catalytic system to be used according to the invention is a bidentate phosphine. In the present context, a bidentate phosphine is intended to cover any organophosphorus compound having at least two phosphine groups and being free of steric hindrance preventing coordination of two phosphine P atoms to a single metal atom. The presence of further coordinating or non-coordinating phosphine groups is not excluded.

Preferred bidentate phosphines to be used according to the present invention have the formula, $$R^1R^2P-X-PR^3R^4 \qquad (I),$$

wherein $R^1$, $R^2$, $R^3$ and $R^4$ independently represent an optionally substituted hydrocarbyl group, or $R^1$ and $R^2$ together and/or $R^3$ and $R^4$ together represent an unsubstituted or substituted bivalent hydrocarbyl group, at least one of $R^1$, $R^2$, $R^3$ and $R^4$ being aliphatic, and X represents a bivalent bridging group having from 2 to about 8 atoms in the bridge. More preferably, each of $R^1$, $R^2$, $R^3$ and $R^4$ independently represents an aliphatic group, such as a substituted or unsubstituted optionally branched or cyclic alkyl group, suitably having from 1 to about 20 carbon atoms Preferred aliphatic groups are unsubstituted alkyl groups which may be branched or cyclic and have from 1 to about 10 carbon atoms, more preferably from 1 to about 6 carbon atoms. Examples of suitable alkyl groups are methyl, ethyl, n-propyl, iso-propyl, n-butyl, sec-butyl, iso-butyl, tert-butyl, cyclohexyl and n-hexyl.

Preferred alkyl groups have one or two alpha-hydrogen atoms, in particular one alpha-hydrogen atom as in secondary alkyl groups. Most preferred alkyl group are ethyl, i-propyl, n-propyl, s-butyl and n-butyl. If together constituting a bivalent hydrocarbyl group, $R^{and}$ $R^2$ or $R^3$ and $R^4$ preferably represent an aliphatic bivalent radical, such as an unsubstituted or substituted alkylene or cycloalkylene group, for example hexamethylene or cyclooctylene.

When the alkyl or alkylene group is said to be optionally substituted, it may be substituted by one or more substituents which do not annihilate the catalytic activity of the system. Suitable substituents include halogen atoms, alkoxy groups, haloalkyl groups, haloalkoxy groups, acyl groups, acyloxy groups, amino groups, hydroxyl groups, nitrile groups, acylamino groups, and aryl groups.

The bridging group represented by X is preferably a hydrocarbon, an ether or a thioether residue. For example, the bridging group may be an optionally substituted alkylene chain which is optionally interrupted by one or more oxygen and/or sulfur atoms, as in:

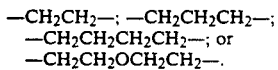

The bridging group preferably contains from 2 to about 6 atoms in the bridge, more preferably from about 3 to about 5 atoms. For example, when the bridging group is a propane or neopentane residue, the bridge contains 3 atoms. Preferred bridging groups X include trimethylene, tetramethylene, and 3-oxapentamethylene.

Examples of phosphines of formula I which may be used in the process according to the invention are:
1,2-bis(di-n-butylphosphino)ethane,
1,3-bis(dimethylphosphino)propane,
1,3-bis(diethylphosphino)propane,
1,3-bis(di-i-propylphosphino)propane,
1,3-bis(di-n-propylphosphino)propane,
1,3-bis(di-i-butylphosphino)propane,
1,3-bis(di-n-butylphosphino)propane,
1,3-bis(di-s-butylphosphino)propane,
1,3-bis(di-t-butylphosphino)propane,
1,3-bis(di-n-hexylphosphino)propane,
1,2-bis(dicyclohexylphosphino)ethane,
1,3-bis(n-butylmethylphosphino)propane,
1,3-bis(n-butylethylphosphino)propane,
1,3-bis(cyclooctylenephosphino)propane,
1,4-bis(di-i-propylphosphino)butane,
1,5-bis(dimethylphosphino)-3-oxapentane,
1,8-bis(di-n-butylphosphino)-3,6-dioxaoctane, and
1,4-bis(di-n-butylphosphino)-2,2,3,3-tetramethylbutane.

The ratio of the number of moles of the phosphine of formula I per gram atom of Group VIII metal is preferably in the range of from about 0.5 to about 10, more preferably from about 0.9 to about 5, especially from 1 to about 3.

It is preferred that the catalytic system to be used in the process of the invention comprises the Group VIII metal in cationic form. The required anion may be generated in situ, or, preferably, is provided as component of the catalyst system. The source of an anion is preferably a protonic acid. However, it may also be a salt of the Group VIII metal, e.g. of palladium. It may also be a salt of another metal, for example vanadium, chromium, nickel, copper or silver.

Preferably the anion is a non- or weakly-coordinating anion: that is to say an anion which does not or only weakly coordinates with the palladium cation. It is preferably derived from a strong acid having a Pka <2, more preferably a Pka< −1 (measured at 18° C. in aqueous solution). Since halide anions, in particular chloride anions, tend to coordinate fairly strong to palladium, the anion preferably is derived from strong acids except hydrohalogenic acids.

For example, the anion may be derived from nitric acid; sulfuric acid; a sulfonic acid such as fluorosulfonic acid, chlorosulfonic acid, methanesulfonic acid, 2-hydroxypropanesulfonic acid, t-butylsulfonic acid, p-toluenesulfonic acid, benzenesulfonic acid, trifluoromethanesulfonic acid, or a sulfonated ion exchange resin; a perhalic acid such as perchloric acid; or an acid derived by the interaction of a Lewis acid, such as $BF_3$, $PF_5$, $AsF_5$, $SbF_5$, $TaF_5$ or $NbF_5$, with a Broensted acid, such as HF (e.g. fluorosilicic acid, $HBF_4$, $HPF_6$, $HSbF_6$).

It will be appreciated that when using a palladium salt of a weak acid, such as acetic acid, the addition of a strong acid such as a sulfonic acid will generate a salt of palladium with the stronger acid, and the weak acid.

The phosphines of formula I as such are known compounds, and can be prepared by general methods described in the literature, for example Houben-Weyl, Vol. XII/I, p.21.

The catalyst system according to the invention is constituted in a liquid phase. It is not necessary to use a separate solvent in the process according to the invention. The starting aldehyde and alcohol product can often form a suitable liquid phase. In some cases, however, it may be desirable to use a separate solvent. Any inert solvent can be used for that purpose. Representative suitable solvents include hydrocarbons, sulfoxides, sulfones, ethers, esters, ketones, alcohols, and amides.

Conveniently, the aldehydes are hydrogenated in the reaction mixture in which they are obtained, for example in the hydroformylation.

Copending application Ser. No. 07/926,534, filed Jul. 13, 1992 discloses the use of a catalyst system comprising a source of palladium cations, a source of bidentate phosphine, and a source of anions derived from a strong acid, inter alia, in the preparation of aldehydes by hydroformylation of olefinically unsaturated compounds.

Accordingly, the same catalyst can be used for both the preparation of an aldehyde by hydroformylation, and subsequent hydrogenation to the corresponding alcohol. Under reaction conditions of fast hydroformylation and slow hydrogenation, the aldehyde may be produced at high concentration in the reaction mixture, from which it could be isolated, if desired. By adapting the reaction conditions to fast hydrogenation, for example by raising the temperature or increasing the hydrogen partial pressure, the intermediate aldehyde is further reacted to the alcohol in the same liquid reaction phase.

By appropriate choice of reaction conditions of fast hydrogenation the alcohol may directly be prepared using the aldehyde precursor olefinically unsaturated compound as starting material. The aldehyde initially formed then is immediately consumed in the hydrogenation reaction to form the alcohol.

The process according to the invention is conveniently effected at a temperature in the range of from about 20° C. to about 200° C., in particular from about 50° C. to about 150° C.

The process according to the invention is preferably effected at a total pressure of from 1 to about 80 bar. Pressures higher than about 100 bar may be used, but are generally economically unattractive on account of special apparatus requirements. A pure hydrogen atmosphere may be used for the hydrogenation, or the hydrogen atmosphere may comprise inert diluent gases. For example, an atmosphere comprising hydrogen and carbon monoxide may be used.

The process according to the invention may be carried out batchwise. Industrially, however, it is advantageous to carry it out continuously.

The alcohols produced by the process of the invention find application as chemical solvent or as precursor for various chemicals.

The invention will now be described by the following Examples which are intended to be illustrative and are not to be construed as limiting the invention.

EXAMPLE 1

A 250 ml magnetically-stirred autoclave was charged with 20 ml propanal, 40 ml diglyme (2,5,8-trioxanonane), 0.25 mmol of palladium acetate, 0.3 mmol of 1,3-bis(di-i-propylphosphino)propane and 1 mmol p-toluenesulfonic acid. After being flushed, the autoclave was pressurized with 60 bar of hydrogen. The autoclave was sealed, heated to a temperature of 90° C., and maintained at that temperature for 15 minutes, whereupon a sample of the contents of the autoclave was analyzed by gas liquid chromatography (GLC). From the results of the analysis it appeared that the propanal had been completely converted into 1-propanol with a selectivity close to 100%. An average rate of conversion of 3900 mol of propanal per gram atom of palladium per hour was observed.

EXAMPLES 2-4

Example 1 was repeated, except for using the phosphines and anion sources in the amounts and for the reaction times mentioned in Table 1 below. The observed conversions of propanal (%), rates of conversion (mol/glr.at.Pd/hr), and selectivities to 1-propanol (%) are reported in the Table.

was pressurized with carbon monoxide and hydrogen up to a partial pressure of 30 bar of each. The autoclave was sealed, heated to a temperature of 70° C., and maintained at that temperature for 7 hours, whereupon GLC of a sample of the contents of the autoclave showed that 80% of the o-octene had been converted into nonyl aldehydes, of which 88% were linear and 12% were linear and 12% were branched.

After cooling the autoclave was flushed, and was then pressurized with 60 bar of hydrogen and heated at 90° C. for 5 hours. GLC analysis showed a 100% conversion of nonyl aldehydes into the corresponding nonyl alcohols at an initial rate of conversion above 300 mol/gr at Pd/hr. The residual octenes remaining after the hydroformylation step, appeared to be substantially unchanged during the hydrogenation, with only 6% being hydrogenated.

EXAMPLE 6 a. A 250 ml magnetically-stirred autoclave was charged with 20 ml α-octene, 40 ml diglyme, 0.25 mmol of palladium acetate, 0.6 mmol of 1,3-bis(di-i-propylphosphino)propane and 1 mmol p-toluenesulfonic acid. After being flushed, the autoclave was pressurized with carbon monoxide and hydrogen up to a partial pressure of 30 bar of each. The autoclave was sealed, heated to a temperature of 90° C., and maintained at that temperature for 5 hours, whereupon GLC analysis of a sample of the contents of the autoclave showed that 67% of the α-octene had been converted with a selectivity of 94% into nonyl aldehydes and 5% into the corresponding nonyl alcohols.

b. The procedure under a. of this Example was repeated charging the autoclave with 15 ml of o-octene and the same solvent and catalytic system. The autoclave was pressurized with 20 bar of carbon monoxide and 40 bar of hydrogen, and heated at 125° C. for 5 hours. GLC analysis showed that 63% of the α-octene had been converted with a selectivity of 88% into nonyl alcohols and 9% into nonyl aldehydes.

It is seen that using the same catalytic system the aldehyde is formed as the predominant product under a., whereas at higher hydrogen pressure and higher

TABLE 1

| Example No. | Gr. VIII Metal (mmol) | Ligand[1] (mmol) | Anion[2] Source (mmol) | Time (hr) | Conversion | Conversion Rate | Selectivity |
|---|---|---|---|---|---|---|---|
| 1 | PdOAc$_2$ (0.25) | iPrPC3 (0.3) | pTSA (1) | 0.25 | 100 | 3900 | 99 |
| 2 | PdPAc$_2$ (0.25) | iPrPC3 (0.3) | pTSA (1) TFAcOH (1) | 0.25 | 98 | 3900 | 99 |
| 3 | PdOAc$_2$ (0.25) | iPrPC3 (0.6) | TFMSA (1) | 0.25 | 100 | 3400 | 99 |
| 4 | PdOAc$_2$ (0.25) | EtPC3 (0.3) | pTSA (1) | 1.5 | 100 | 900 | 99 |

[1])PrPC3: 1,3-bis(di-i-propylphosphino)propane;
EtPC3: 1,3-bis(diethylphosphino)propane;
[2]pTSA: p-toluene sulfonic acid;
TFAcOH: trifluoro acetic acid;
TFMSA: trifluoromethylsulfonic acid;
PhPA: benzenephosphonic acid

EXCAMPLE 5

A 250 ml magnetically-stirred autoclave was charged with 20 ml α-octene, 40 ml diglyme (2,5,8-trioxanonane), 0.25 mmol of palladium acetate, 0.6 mmol of 1,3-bis(di-i-propylphosphino)propane and 1 mmol t-butylsulfonic acid. After being flushed, the autoclave temperature the alcohol is the predominant product under b. Apparently, in both experiments the aldehyde is formed in a first reaction step and subsequently consumed as a starting material for the second hydrogenation step, under a. at relatively low rate and under b. at relatively high rate under conditions of temperature and hydrogen concentration favorable for hydrogenation.

EXAMPLE 7

Following generally the procedure of Example 6b., a 250 ml magnetically-stirred autoclave was charged with 20 ml α-dodecene, 40 ml diglyme, 0.25 mmol of palladium acetate, 0.6 mmol of 1,3-bis(1,5-cyclooctylenephosphino)propane, 1 mmol p-toluenesulfonic acid and 1 mmol trifluoro acetic acid. The autoclave was pressurized with 20 bar of carbon monoxide and 40 bar of hydrogen, and heated at 125 °C. for 5 hours. It was found that 62% of the o-dodecene had been converted with a selectivity of 98% into tridecyl alcohols and traces of the corresponding aldehydes.

EXAMPLE 8

As in the previous Example, a 250 ml magnetically-stirred autoclave was charged with 30 ml of a mixture of internally unsaturated $C_{14}$ olefins, 40 ml diglyme, 0.5 mmol of palladium acetate, 1.2 mmol of 1,3- bis(di-i-propylphosphino)propane, 2 mmol p toluenesulfonic acid and 1 mmol trifluoro acetic acid. The autoclave was pressurized with 20 bar of carbon monoxide and 40 bar of hydrogen, and heated at 155° C. for 10 hours. It was found that 71% of the $C_{14}$ olefins had been converted with a selectivity of 98% into pentadecyl alcohols.

EXAMPLE 9

As in the previous Example, a 250 ml magnetically-stirred autoclave was charged with 20 ml cyclohexene, 50 ml diglyme, 0.25 mmol of palladium acetate, 0.6 mmol of 1,3-bis(dimethylphosphino)propane, 1 mmol trifluoro acetic acid and 1 mmol p-toluenesulfonic acid. The autoclave was pressurized with 20 bar of carbon monoxide and 40 bar of hydrogen, and heated at 130° C. for 5 hours. It was found that 6% of the cyclohexene had been converted with a selectivity of 99% into cyclohexylmethanol.

EXAMPLE 10

As in the previous Example, a 250 ml magnetically-stirred autoclave was charged with 20 ml styrene, 50 ml diglyme, 0.25 mmol of palladium acetate, 0.6 mmol of 1,3-bis(di-i-propylphosphino)propane and 1 mmol p-toluenesulfonic acid. The autoclave was pressurized with 20 bar of carbon monoxide and 40 bar of hydrogen, and heated at 125° C. for 5 hours. It was found that 90% of the styrene had been converted with a selectivity of 85% 3-phenyl-1-propanol and 15% into 2-phenyl-1-propanol.

What is claimed is:

1. A process for the preparation of an alcohol which comprises hydrogenating an aldehyde at a temperature in the range of from about 20° C. to about 200° C. and superatmospheric pressure in the presence of a homogeneous catalytic system comprising a source of Group VIII medal compound wherein said Group VIII metal is selected from the group consisting of palladium, platinum, rhodium, and mixtures thereof, and a bidentate phosphine having a general formula: $R^1R^2P—X—PR^3R^4$ wherein $R^1$, $R^2$, $R^3$, $R^4$ independently represent an unsubstituted or substituted hydrocarbyl group, or $R^1$ and $R^2$ together and/or $R^3$ and $R^4$ together represent an unsubstituted or substituted bivalent hydrocarbyl group, at least one of $R^1$, $R^2$, $R^3$, and $R^4$ being aliphatic, and X represents a bivalent bridging group having from 2 to about 8 atoms in the bridge.

2. The process as claimed in claim 1, wherein the Group VIII metal is palladium.

3. The process as claimed in claim 1, wherein in formula I each of $R^1$, $R^2$, $R^3$ and $R^4$ independently represents a substituted or unsubstituted branched or cyclic alkyl group having from 1 to about 10 carbon atoms.

4. The process as claimed in claim 1, wherein in formula I at least one of $R^1$, $R^2$, $R^3$ and $R^4$ represents an unbranched or branched cyclic alkyl group having one or two alpha hydrogen atoms.

5. The process as claimed in claim 4, wherein in formula I at least one of $R^1$, $R^2$, $R^3$ and $R^4$ represents a secondary alkyl group.

6. The process as claimed in 1, wherein in formula I, X represents an alkylene chain which is interrupted by one or more oxygen and/or sulfur atoms.

7. The process as claimed in claim 6, wherein X represents a trimethylene, tetramethylene or 3-oxapentamethylene chain.

8. The process as claimed in claim 1, wherein the catalytic system further comprises a source of anions derived from a strong acid.

9. The process as claimed in claim 8, wherein the anions are derived from an acid having a pKa below −1.

10. The process as claimed in claim 1, wherein an aldehyde which has been prepared by hydroformylation of an olefinically unsaturated compound is used as starting material.

11. The process as claimed in claim 10, wherein the aldehyde starting material is prepared in situ and without isolation is hydrogenated to the alcohol.

12. The process as claimed in claim 11, wherein the aldehyde starting material is prepared in the presence of a homogeneous catalyst system comprising a source of a Group VIII metal compound and a bidentate phosphine.

* * * * *